United States Patent [19]

Arakelian, Sr.

[11] Patent Number: Plant 6,230

[45] Date of Patent: Jul. 26, 1988

[54] PEACH TREE

[76] Inventor: Haig Arakelian, Sr., Rte. 7, 829 Church St., Modesto, Calif. 95351

[21] Appl. No.: 896,713

[22] Filed: Aug. 15, 1986

[51] Int. Cl.[4] ..... A01H 5/03

[52] U.S. Cl. ..... Plt./43

[58] Field of Search ..... Plt./43

*Primary Examiner*—Robert E. Bagwill

*Attorney, Agent, or Firm*—Worrel & Worrel

[57] ABSTRACT

A new and distinct variety of peach tree which is characterized by fruit which is clingstone in nature and which has a flesh which is bright yellow in color and which is ripe for commercial harvesting from July 27 to August 1 in Modesto, Calif.

1 Drawing Sheet

BACKGROUND OF THE INVENTION

The present invention relates to a new and distinct variety of peach tree denominated varietally as "Haig Arakelian, Sr." and more particularly to such a peach tree which bears a clingstone fruit which has a non-melting flesh texture, which is bright yellow in color and which is additionally characterized as to novelty by a date of ripening of approximately July 27 through August 1, in Modesto, Calif.

From an economic perspective, the relative dates that various varieties of peaches become ripe for harvesting is of extreme importance to the owners of orchards of stone fruits. It has long been recognized as desirable to provide a peach tree that bears fruit during a portion of the season later than other varieties of peach trees, which it most nearly resembles, whereby the fruit can be sent to market at a time when competition is at a minimum and the best price can be negotiated. It should be understood that an additional economic benefit is attached if the harvesting period of a particular orchard is spread over a longer period of time, because the capital expenditure required to harvest and transport produce from the orchards can be spread over an extended period resulting in overall lower costs of the final product and increasing uniformity of production throughout an entire season.

The new and distinct variety of peach tree is characterized as to novelty by producing a peach which matures for harvesting at mid-season; approximately July 27 through August 1 in Modesto, Calif., and in addition has demonstrated a greater fruit sizing potential than other varieties to which it is most closely similar.

ORIGIN AND ASEXUAL REPRODUCTION OF THE NEW VARIETY

The new and distinct variety of peach tree of the present invention is of unknown origin, and was discovered by the applicant in a cultivated area of his orchard which is located at the corner of Church and Garst Streets, Modesto, Calif. The new variety, which was first observed in July, 1979, during routine orchard operations, was asexually reproduced by taking budwood from the subject tree and thereafter budding it on Nemaguard peach rootstock. This procedure took place in May of 1984. The budded trees have been constantly observed by the applicant and it has been determined that the progeny produced possess the same distinctive characteristics as the parent tree.

Inasmuch as the prevent variety's precise origin is unknown, it was known by the applicant in the sense that he discovered the new variety of peach tree in a cultivated area owned by him, recognized its distinctive qualities, asexually reproduced the same, and tested the subject seedling at the designated orchard located at the corner of Church and Garst Streets, Modesto, Calif.

BRIEF DESCRIPTION OF THE DRAWINGS

The accompanying drawing is a color photograph of a characteristic twig bearing typical leaves which display both the dorsal and ventral coloration; four peaches showing their external colorations sufficiently matured for harvesting and shipment; a peach halved transversely of the suture plane to illustrate the flesh coloration; and a stone, all of the subject variety.

DETAILED DESCRIPTION

Referring more particularly to the pomological details of the new and distinct variety of peach tree the following has been observed under the ecological conditions prevailing in the orchard of the inventor in Modesto, Calif. All major color code designations are by reference to *The Dictionary of Color* by Maerz and Paul published in 1950, common color names are also used in several instances.

TREE

Size: Average.

Upright, and spreading, with form and density determined by pruning practices.

Vigor: Vigorous.

Productivity: Very productive.

Regularity of bearing: Regular; the new variety is hardy under typical San Joaquin Valley climatic conditions.

Trunk:

- *Bark texture.*—Medium.
- *Size.*—Average in thickness.
- *Color.*—*Gray,* (7-C-7).
- *Lenticels.*—Numbers — numerous; size — medium to large.

Branches:

- *Size.*—Average.
- *Texture.*—Medium.
- *Color.*—Mature branches — light brown, to grayish brown, (7-*E*-10) through (7-C-9).
- *Color.*—Young branches — grayish green, (21-H-4).
- *Lenticels.*—Numbers — few.

LEAVES

Size: Medium.

*Average length.*—Approximately 145 mm.

*Average width.*—34 mm.

Form:

*Leaf.*—Lanceolate; tip — acuminate; the leaf is often curved and twisted to one side.

Color:

*Dorsal surface.*—Dark green, (24-L-5).

*Ventral surface.*—Grayish green, (22-D-4).

Margin:

*Generally.*—Crenate, although the leaf may occasionally display a doubly crenate form along its basal margin. The variety displays a finely crenate form along the margin of the leaf tip.

Edge: Strongly undulate; new leaves are crinkled in appearance.

Petiole:

Size.—Medium; length — approximately 9 to 10 mm.

*Thickness.*—Approximately 1 to 1.5 mm.

*Color.*—Light greenish yellow, (18-G-4); the petiole grooves are slightly darker.

Glands:

*Form.*—Globose; numbers — generally 2 to 3.

*Size.*—Small; color — light green, (20-K-4). The glands appear somewhat more luster on a young leaf. The glands darken and deteriorate with age.

*Position.*—Alternate; the glands are found at the base of the leaf margin and commonly with one or two located directly on the petiole.

Stipules:

*Length.*—Moderately long; the stipules may attain a length of 8 mm.

*Numbers.*—Generally 2; the stipules are located at the base of the petiole.

*Color.*—Light green, (20-J-5). This color is typically observed when the leaf is young. The color however quickly darkens and becomes brown, with increased age. The tree is most properly classified as a moderately early deciduous.

Flower buds:

*Size.*—Medium.

*Length.*—Average.

*Color.*—Grayish brown, (7-C-7).

*Shape.*—Conic.

*Pubescence.*—Average; the flower buds are hardy for California climatic conditions.

Flowers:

*Date of full Bloom.*—Approximately March 11 in Modesto, Calif.; the date of bloom is average as compared with other varieties which bloom in the area of Modesto, Calif.

*Size.*—Small.

*Diameter.*—Approximately 18 to 21 mm.

*Flower type.*—Non-showy. The flowers of the subject variety are one of the largest of this particular blossom form.

*Bloom.*—Abundant; each node produces one to three flowers.

*Petals.*—Size — small. Shape — slightly ovate. Length — approximately 10 to 11 mm. Width — approximately 9 to 10 mm. Color — light pink, (49-C-1). This color is slightly darker along the petal margin, (49-H-3).

FRUIT

Maturity for harvest: Approximately July 27 to August 1 in Modesto, Calif.

Size: Generally — medium to large.

*Average diameter in the suture plane.*—Approximately 65.6 mm.

*Average diameter in the cheek plane.*—Approximately 65.4 mm.

*Average axial diameter.*—Approximately 63.1 mm.

*Uniformity.*—Very good. The variety produces fruit with less than average size variations.

Form:

*Uniformity.*—Uniform.

*Symmetry.*—Symmetrical; one-half the fruit is usually larger, but only somewhat slightly so.

*Shape.*—Globose in its basal aspect and very regular; nearly globose in its lateral aspect, only occasionally slightly oblate.

*Suture.*—The suture appears as a narrow inconspicuous line extending from the base to the apex and on some occasions, 5 to 15 mm. beyond the pistil point. The suture has a marked depression beyond the pistil point. The suture's coloration causes it to blend in well with the underlying ground or blush color. Only occasionally will the suture display a slight red stripping in the suture crease; Color — (4-K-9).

Ventral surface:

*Shape.*—Rounded, and very slightly lipped on both sides. The lips, when they are present, are usually equal.

Stem cavity:

*Depth.*—Moderately deep, approximately 10 to 11 mm.

*Shape.*—Basal aspect-oblong in the suture plane. The sutures of large numbers of the subject variety are visible for a depth of 5 to 8 mm. on the dorsal side of the stem attachment.

*Width.*—Approximately 15 to 22 mm.

*Length.*—Approximately 24 to 27 mm.

Base:

*Shape.*—Rounded; occasionally it may appear slightly truncate. The base is most often at a right-angle to the fruit axis.

*Length.*—Medium, approximately 8 to 10 mm.

*Thickness.*—Approximately 2.5 to 3 mm.

*Color.*—Light green, (20-K-6).

Apex:

*Shape.*—Rounded.

*Length.*—Short, with the pistil point most often depressed, although occasionally the pistil point may be raised. The pistil point is oblique to the fruit axis.

Skin:

*Thickness.*—Average.

*Texture.*—Medium.

*Tenacious to flesh.*—Yes.

*Tendency to crack.*—Not observed.

*Pubescence.*—Slight to medium.

*Fibers.*—Length — moderately short.

*Color.*—Ground color — straw yellow, (10-I-30). This color is found on 80% to 95% of the fruit surface.

*Blush color.*—Reddish orange, (3-H-10), occasionally a light red dappled striping, (3J-11) may be found. The foregoing colors may cover up to 15% of the fruit surface.

*Flesh color.*—Yellow (10-K-5), a slightly darker yellow amber color may be found at the center of the fruit, (10-K-7). There is no red coloration found at the pit.

*Amygdalin.*—Slight to lacking.

*Juice production.*—Moderately juicy.

*Flavor.*—Very good; well-balanced.

*Aroma.*—Moderate; pleasant.

*Flesh texture.*—Non-melting; dense; firm; fine textured.

*Fibers.*—Numbers — few; short in length, and fine textured.

*Ripening.*—Even.

*Eating quality.*—Above average.

Stone:

*Freestone or clingstone.*—Full clingstone.

*Size.*—Generally small to medium. average length — approximately 38 mm. average width — approximately 28 mm. average thickness — approximately 21 mm.

*Fibers.*—Numbers — average for clingstone type peaches; length — medium.

*Form.*—Obovate.

*Base.*—Positioned at right angles to the stone axis.

*Hilum.*—Shape — oval; size — moderately large, at times the stone appears heavily eroded.

*Apex.*—Acute; the tip is acuminate.

*Sides.*—Variable; sides may appear equal or very slightly unequal.

*Stone surface.*—Generally very rough; deeply grooved and ridged over the lateral surfaces. The grooves are especially deep over the basal shoulders. Ridges are quite prominent over the apical shoulders.

*Pits.*—Numbers — few in number and very deep. The pits are usually located laterally at mid-stone.

*Ventral edge.*—Low. The stone has a moderately wide wing which converges apically.

*Dorsal edge.*—The stone has two thick ridges that subtend a moderately wide groove which becomes more shallow basally and apically. Apical shoulders are moderately eroded.

*Stone color.*—Dry — buff, (11-E-5).

*Tendency to split.*—Not observed.

Use: Commercial canning.

Keeping quality: The fruit of the subject variety hangs well on the tree even at commercial maturity.

Resistance to insects and disease: No particular susceptibilities noted.

Although the new variety of peach tree prossesses the described characteristics as a result of the growing conditions prevailing in Modesto, Calif. in the north-central portion of the San Joaquin Valley, it is to be understood that variations of the usual magnitude and characteristics incident to growing conditions, fertilization, pruning and pest control are to be expected.

Having thus described my new variety of Peach Tree, what I claim as new and what I desire to secure by Letters Patent is:

1. A new distinct variety of peach tree substantially as illustrated and described which produces full clingstone peaches which have a flesh which is non-melting in texture and bright yellow in color, which has demonstrated a greater fruit sizing potential than other varieties to which it is most closely similar, and whose fruit are ripe for harvesting from July 27 through August 1.

* * * * *

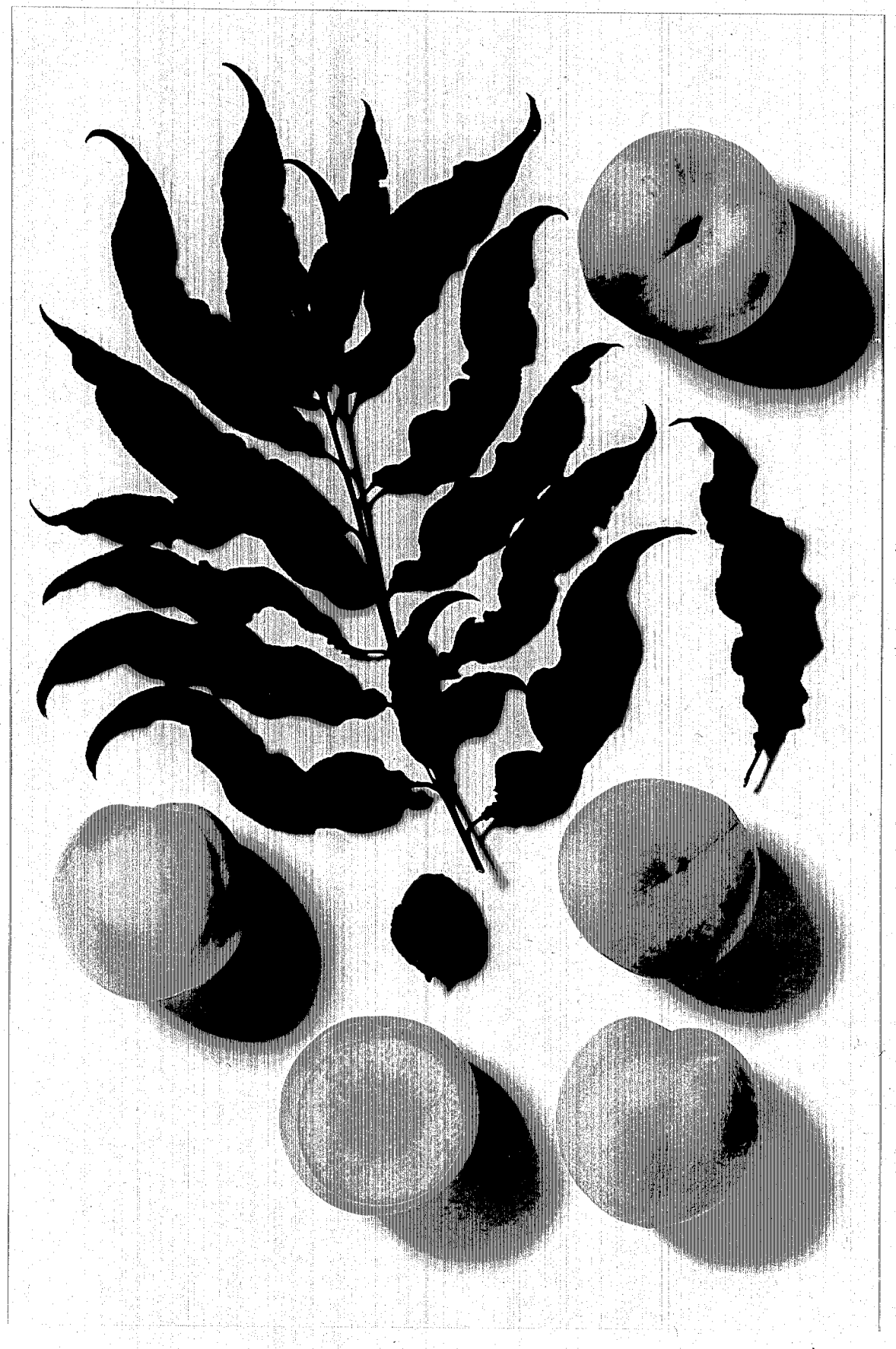

UNITED STATES PATENT AND TRADEMARK OFFICE

CERTIFICATE OF CORRECTION

PATENT NO. : Plant 6,230

DATED : July 26, 1988

INVENTOR(S) : Haig Arakelian, Sr.

It is certified that error appears in the above-identified patent and that said Letters Patent is hereby corrected as shown below:

Column 2, line 1, delete "prevent" and substitute ---present---.

Column 4, line 66, delete (3J-11) and substitute ---(3-J-11).

Signed and Sealed this

Twenty-ninth Day of November, 1988

*Attest:*

DONALD J. QUIGG

*Attesting Officer*

*Commissioner of Patents and Trademarks*